US012721877B2

(12) United States Patent
Ooi

(10) Patent No.: US 12,721,877 B2
(45) Date of Patent: Sep. 1, 2026

(54) PHARMACEUTICAL COMPOSITION FOR CONDITIONING DAMPNESS-HEAT

(71) Applicant: Wei Zhi Ooi, Ampang (MY)

(72) Inventor: Wei Zhi Ooi, Ampang (MY)

( * ) Notice: Subject to any disclaimer, the term of this patent is extended or adjusted under 35 U.S.C. 154(b) by 365 days.

(21) Appl. No.: 18/502,012

(22) Filed: Nov. 5, 2023

(65) Prior Publication Data

US 2024/0382547 A1 Nov. 21, 2024

(51) Int. Cl.

| | |
|---|---|
| ***A61K 36/484*** | (2006.01) |
| ***A61K 9/00*** | (2006.01) |
| ***A61K 36/185*** | (2006.01) |
| ***A61K 36/233*** | (2006.01) |
| ***A61K 36/355*** | (2006.01) |
| ***A61K 36/482*** | (2006.01) |
| ***A61K 36/535*** | (2006.01) |
| ***A61K 36/536*** | (2006.01) |
| ***A61K 36/539*** | (2006.01) |
| ***A61K 36/605*** | (2006.01) |
| ***A61K 36/634*** | (2006.01) |
| ***A61K 36/65*** | (2006.01) |
| ***A61P 43/00*** | (2006.01) |

(52) U.S. Cl.

CPC ............ *A61K 36/484* (2013.01); *A61K 9/009* (2013.01); *A61K 36/185* (2013.01); *A61K 36/233* (2013.01); *A61K 36/355* (2013.01); *A61K 36/482* (2013.01); *A61K 36/535* (2013.01); *A61K 36/536* (2013.01); *A61K 36/539* (2013.01); *A61K 36/605* (2013.01); *A61K 36/634* (2013.01); *A61K 36/65* (2013.01); *A61P 43/00* (2018.01)

(58) Field of Classification Search

CPC .... A61K 36/484; A61K 9/009; A61K 36/185; A61K 36/233; A61K 36/355; A61K 36/482; A61K 36/535; A61K 36/536; A61K 36/539; A61K 36/605; A61K 36/634; A61K 36/65; A61P 43/00

See application file for complete search history.

(56) References Cited

U.S. PATENT DOCUMENTS

2007/0122492 A1* 5/2007 Behr .................... A61K 8/9789 424/754

FOREIGN PATENT DOCUMENTS

| | | | | |
|---|---|---|---|---|
| CN | 107823404 A | * | 3/2018 | ........... A61K 36/195 |
| CN | 108114140 A | * | 6/2018 | ........... A61K 36/538 |

OTHER PUBLICATIONS

English translation of CN CN 108114140 A from EPO. (Year: 2025).*

English translation of CN 107823404 A from EPO. (Year: 2025).*

* cited by examiner

*Primary Examiner* — Michael P Cohen

(57) ABSTRACT

The present invention relates to a pharmaceutical composition for conditioning dampness-heat. The pharmaceutical composition consists of licorice root, forsythia shell, tree peony root bark, baical skullcap root, cassia twig, root of Chinese thorowax, *Oroxylum indicum* seed, mulberry leaf, prunella vulgaris, honeysuckle and perilla leaf. Herein, ratio of the licorice root to forsythia shell to tree peony root bark to baical skullcap root to cassia twig to root of Chinese thorowax to *Oroxylum indicum* seed to mulberry leaf to prunella vulgaris to honeysuckle and to perilla leaf is about 3:10:10:10:8:10:2:10:5:7:3.

11 Claims, No Drawings

PHARMACEUTICAL COMPOSITION FOR CONDITIONING DAMPNESS-HEAT

FIELD OF THE INVENTION

The present invention relates to a pharmaceutical composition. More particularly, the present invention relates to a pharmaceutical composition having a function for conditioning dampness-heat.

BACKGROUND ART

In Traditional Chinese Medicine (TCM), an imbalance in the Yin and Yang energy of the body is frequently linked to increased body heat. Yang energy is warm and energising, whereas Yin energy is chilly and soothing. Fever, thirst, irritation, and perspiration are some of the signs of an excess of Yang energy in the body. To reduce excessive heat, TCM practitioners may recommend herbs that have cooling properties, such as chrysanthemum, mint, and honeysuckle. These plants are believed to increase Qi flow and remove heat from the body. Acupuncture is another method, involving the insertion of tiny needles into certain body locations in order to promote Qi flow and balance the body's energy systems. Fever, headaches, and irritation are a few of the specific symptoms of excessive heat that can be treated with acupuncture. Dietary modifications may also be suggested by TCM practitioners to assist lower body heat. This may entail staying away from hot or oily foods, which are thought to increase body heat, and eating more cool foods instead, such as cucumber, watermelon, and mung beans. The term "Qi" (pronounced "chee") refers to the life force that permeates the body in Traditional Chinese Medicine (TCM). The movement of this energy throughout the body is known as qi flow. In TCM, meridians are seen as paths or channels through which Qi flows. It is thought that these meridians connect the organs, muscles, and tissues of the body to other regions of the body. These meridians are said to improve health and well-being when Qi runs through them smoothly. Qi flow disruptions can cause the body to become unbalanced and result in a number of different health issues. For instance, if a meridian is blocked, Qi could get stagnant and cause discomfort, inflammation, or other symptoms.

In recent times, Chinese herbs have gained significant attention for their potential medicinal properties and lack of negative side effects. Heat-clearing Chinese herbs (HCCHs) are a particular class of these Chinese herbs that are thought to have cooling characteristics and can help reduce inflammation, toxicity, and heat removal. Due to their potent anti-inflammatory and anti-microbial properties, they are a flexible class of herbs that can be used to treat a variety of medical ailments. Traditional Chinese Medicine (TCM) often uses HCCHs in decoction form. However, this method of treatment can present challenges due to its complicated preparation process, undesirable taste, limited solubility, and inconsistent chemical composition. Additionally, if the decoction requires a long preparation time, it may be challenging for patients to maintain regular consumption. For example, a Chinese patent publication document CN105395941A published on 16 Mar. 2016 discloses a heat-clearing and detoxifying traditional Chinese medicine oral liquid. The liquid for oral consumption is prepared using the following ingredients: 9 g of mulberry leaf, 9 g of chrysanthemum flower, 12 g of dyers woad leaf, 12 g of weeping forsythia capsule, 6 g of mint, 20 g of gypsum, 15 g of common anemarrhena rhizome, 15 g of reed rhizome, 12 g of snake gourd fruit, 9 g of bamboo shavings, 12 g of platycodon root, 9 g of tendril leaf fritillary bulb, 10 g of cassia twig, 9 g of ephedra, 9 g of fine leaf schizonepeta herb, 6 g of stir-fried bitter apricot seed, and 12 g of licorice root. The preparation method involves measuring the above traditional Chinese medicinal ingredients, boiling them with 1500 ml of water on low heat for 45 minutes, straining the liquid to obtain medicine, cooling it, adding 30 mL of honey, and thoroughly mixing it. The oral liquid is divided into two parts, with one taken in the morning and the other at night. The course of treatment lasts three days.

Therefore, the present invention aims to overcome the limitations of Heat-clearing Chinese herbs (HCCHs) used in decoction form by introducing a synergistic pharmaceutical composition that effectively alleviates the symptoms of dampness-heat.

SUMMARY OF THE INVENTION

Aspects of the present disclosure are to address the above-mentioned problems and or disadvantages and to provide at least the advantages described throughout this patent specification.

Accordingly, an aspect of the present disclosure is to provide a pharmaceutical composition for conditioning dampness-heat consisting of licorice root, forsythia shell, tree peony root bark, baical skullcap root, cassia twig, root of Chinese thorowax, *Oroxylum indicum* seed, mulberry leaf, prunella vulgaris, honeysuckle and perilla leaf.

Another aspect of the present disclosure is to provide the pharmaceutical composition, wherein ratio of said licorice root to said forsythia shell to said tree peony root bark to said baical skullcap root to said cassia twig to said root of Chinese thorowax to said *Oroxylum indicum* seed to said mulberry leaf to said prunella vulgaris to said honeysuckle and to said perilla leaf is about 3:10:10:10:8:10:2:10:5:7:3.

Another aspect of the present disclosure is to provide the pharmaceutical composition, wherein said licorice root, said forsythia shell, said tree peony root bark, said baical skullcap root, said cassia twig, said root of Chinese thorowax, said *Oroxylum indicum* seed, said mulberry leaf, said prunella vulgaris, said honeysuckle and said perilla leaf is a heated licorice root, heated forsythia shell, heated tree peony root bark, heated baical skullcap root, heated cassia twig, heated root of Chinese thorowax, heated *Oroxylum indicum* seed, heated mulberry leaf, heated prunella vulgaris, heated honeysuckle and heated perilla leaf.

Another aspect of the present disclosure is to provide the pharmaceutical composition, wherein said pharmaceutical composition as a whole further contains 10 wt. % of sweeteners selected from the group consisting of sugar, honey or stevia.

Another aspect of the present disclosure is to provide the pharmaceutical composition, wherein said pharmaceutical composition is an oral composition.

Another aspect of the present disclosure is to provide the pharmaceutical composition, wherein said pharmaceutical composition is formulated in the form of tablets, capsules, tea bags or sachets.

Another aspect of the present disclosure is to provide the pharmaceutical composition, wherein said tablets further include an outer protective coating or finishing layer surrounding said tablets.

Another aspect of the present disclosure is to provide the pharmaceutical composition, wherein said tablets having a weight from about 4 grams to about 6 grams.

Another aspect of the present disclosure is to provide the pharmaceutical composition, wherein said capsules having a weight from about 250 milligrams to about 280 milligrams or from about 500 milligrams to about 550 milligrams.

Another aspect of the present disclosure is to provide the pharmaceutical composition, wherein said tea bags having a weight of about 2 grams.

Another aspect of the present disclosure is to provide the pharmaceutical composition, wherein said sachets having a weight of about 15 milliliters.

Another aspect of the present disclosure is to provide the use of the pharmaceutical composition in the preparation of a medicament for use in the treatment of dampness-heat by oral administration.

Another aspect of the present disclosure is to provide a method for the treatment of dampness-heat by oral administration, the method comprising administering to a subject in need of such treatment an effective amount of the pharmaceutical composition.

Another aspect of the present disclosure is to provide the method for the treatment of dampness-heat by oral administration, wherein said subject includes a human.

DETAILED DESCRIPTION

While embodiments of this invention can take many different forms, the preferred embodiments will be described herein in detail with the understanding that the present invention is to be considered as an exemplification of the principles of the invention, as well as the best mode of practicing same, and is not intended to limit the invention to the specific embodiment illustrated.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purposes only and not for the purpose of limiting the present disclosure as defined by the appended claims and their equivalents. Depending on the context of the sentence, the reading of this patent specification should be done with the same concept as "reject the absurd", wherein if possible, a specification should be construed so as not to lead to a foolish result or one which the patentee could not have contemplated.

The term "about" as used herein, the particular value as determined by one skilled in the art (values depend on the manner in which is measured or determined), an acceptable error range, that is, the measuring system means that therein within the limits. For example, "about" can mean within standard deviations above the 1 or 1 per practice in the art. If a specific value is set forth in the application and claims, unless otherwise stated, the term "about" means within an acceptable error range for the particular value. If rigidity is needed in interpreting this term, in this application, the term about may be suggested as +5% of the given value or can be considered as a range of effective value.

The term "dampness-heat" in the context of traditional Chinese medicine describes an internal imbalance within the body characterized by the coexistence of dampness and heat. Heat is an excessive, inflammatory quality characterized by symptoms like fever and inflammation, whereas dampness is a heavy, stagnant quality in the body that is frequently linked with fluid retention. Heat and moisture can jointly result in a number of symptoms, including fatigue, skin rashes, joint discomfort, and digestive problems. Treatment in traditional Chinese medicine often involves addressing the underlying imbalance through the use of herbs, acupuncture, dietary changes, and lifestyle modifications.

As used in this specification and the appended claims, the singular forms "a", "an", and "the" encompass embodiments having plural referents, unless the content clearly dictates otherwise. As used in this specification, the use of a singular form of a term can encompass embodiments including more than one of such terms, unless the context clearly dictates otherwise. As used in this specification and the appended claims, the term "or" is generally employed in its sense including "either or both" unless the context clearly dictates otherwise.

The present invention provides a pharmaceutical composition for conditioning dampness-heat, consisting of, as active ingredients, a combination of licorice root, forsythia shell, tree peony root bark, baical skullcap root, cassia twig, root of Chinese thorowax, *Oroxylum indicum* seed, mulberry leaf, prunella vulgaris, honeysuckle, and perilla leaf. These active ingredients are preferably heated prior to use in the preparation of the pharmaceutical composition, with licorice root, forsythia shell, tree peony root bark, baical skullcap root, cassia twig, root of Chinese thorowax, *Oroxylum indicum* seed, mulberry leaf, prunella vulgaris, honeysuckle, and perilla leaf being preferably heated licorice root, heated forsythia shell, heated tree peony root bark, heated baical skullcap root, heated cassia twig, heated root of Chinese thorowax, heated *Oroxylum indicum* seed, heated mulberry leaf, heated prunella vulgaris, heated honeysuckle, and heated perilla leaf, respectively. The composition preferably includes the active ingredients in the ratio of about 3:10:10:10:8:10:2:10:5:7:3 for licorice root, forsythia shell, tree peony root bark, baical skullcap root, cassia twig, root of Chinese thorowax, *Oroxylum indicum* seed, mulberry leaf, prunella vulgaris, honeysuckle, and perilla leaf, respectively. The following Table 1 shows the proportion of each active ingredient used in the preparation of the composition of the present invention.

TABLE 1

Formulations of the composition of the present invention

| Active Ingredients | Gram | Percentage |
|---|---|---|
| Licorice Root | 300 | 3.8% |
| Forsythia Shell | 1000 | 12.8% |
| Tree Peony Root Bark | 1000 | 12.8% |
| Baical Skullcap Root | 1000 | 12.8% |
| Cassia Twig | 800 | 10.3% |
| Root of Chinese Thorowax | 1000 | 12.8% |
| *Oroxylum indicum* seed | 200 | 2.6% |
| Mulberry Leaf | 1000 | 12.8% |
| Prunella Vulgaris | 500 | 6.4% |
| Honeysuckle | 700 | 9.0% |
| Perilla Leaf | 300 | 3.8% |

According to the present invention, the combination of these active ingredients is found to work together synergistically to alleviate the symptoms of dampness-heat. Symptoms of dampness-heat may vary depending on the affected area of the body. For instance, eczema or malignant boil may occur if dampness-heat affects the skin and flesh; whereas joint pain, tendon, and vessel swelling may occur in other cases. However, dampness-heat usually pertains to internal organs, particularly in the spleen and stomach, where it is manifested as epigastric oppression and fullness of the abdomen, nausea and anorexia, loose stool, short and red urine, and soft pulse. Dampness-heat may also affect other organs, such as the liver and gallbladder, bladder, and intestine, with corresponding symptoms. The composition of the present invention effectively eliminates the causes of dampness-heat conditions with predominant heat by removing heat and toxic matter, regulating the middle energizer to descend qi, and promoting diuresis. Herein, the use of Chinese thorowax roots improves liver function by eliminating toxins from the body. Baical skullcap root and forsythia shell reduce swelling and inflammation, while mulberry leaf and tree peony root bark reduce inflammation, cholesterol, and blood sugar. Honeysuckle and cassia twig promote urination and sweating to eliminate toxins from the body, while also providing antipyretic, antifungal, and antibacterial effects. Licorice and perilla leaf address heart-related inflammation, and prunella vulgaris heal throat infections. By conditioning the dampness-heat with the composition of the present invention, individuals may become more resistant to diseases, with reduced occurrences of ailments. The composition of the present invention offers a targeted approach to condition dampness-heat, making individuals more resistant to diseases, with reduced occurrences of ailments. Moreover, the composition is free from side effects and does not harm the human body, thus effectively strengthening the body without any adverse effects.

The active ingredients used in the composition have a long history of traditional use in treating various ailments. Licorice root, for example, is used to treat heartburn, acid reflux, hot flashes, coughs, and bacterial and viral infections. Forsythia is used for airway illnesses, swelling, fever, and other conditions. Peony might block chemicals that can cause pain and swelling, and it might also prevent blood clotting, kill cancer cells, and act as an antioxidant. Baikal skullcap is a plant native to China and Korea, and its root has been used in Chinese medicine for psychiatric disorders, as it contains chemicals that might decrease swelling and stop tumor growth. Cassia twig benefits healthy digestion, promotes normal blood glucose levels when used as part of a healthy diet along with exercise, supports cardiovascular health, and may benefit joint health. It also has anti-inflammatory, antipyretic, antifungal, and antibacterial effects. The root of Chinese thorowax is an important medicinal herb to help cleanse the liver and stimulate the immune system, while *Oroxylum indicum* seed has been used to treat heart issues and constipation. Mulberry leaves may help lower blood sugar, cholesterol, and inflammation levels, and Prunella vulgaris is known as "heal-all" due to its traditional use in healing wounds, throat infections, and several other ailments. Honeysuckle is also used for urinary disorders, headache, diabetes, rheumatoid arthritis, and cancer. Finally, perilla leaf is used for a wide range of inflammatory conditions, heart diseases, colitis/Crohn's disease, asthma, allergies, antimicrobial, anticancer, and other health concerns.

The present invention also provides a pharmaceutical composition for use in the treatment of dampness-heat by oral administration, as well as a method for administering the composition to a subject in need of such treatment. The method includes administering an effective amount of the composition to a human subject for the treatment of dampness-heat by oral administration. The composition for oral administration comprises therapeutically active ingredients that enable the patient to retain the composition in their mouth, facilitating the delivery of the active ingredients through the oral mucosa as described above. This type of formulation is well-known in the pharmaceutical industry for its effectiveness.

The composition may incorporate a pharmaceutically acceptable carrier. The carrier facilitates the application or dissemination of the active ingredient to the targeted site and allows for storage, transport, or handling without compromising its efficacy. The composition may exist in various forms, such as concentrates, emulsions, solutions, granulates, dusts, pellets, or powders, with the carrier being a solid, liquid, or compressed gas. Pharmaceutical carriers that are suitable for use in the composition and formulation thereof are well-known to those skilled in the art. There are no particular restrictions on the selection of carriers within the scope of this invention. In addition, the composition may include additives such as wetting agents, dispersing agents, stickers, adhesives, emulsifying agents, solvents, coatings, antibacterial and antifungal agents (e.g., phenol, sorbic acid, chlorobutanol), isotonic agents (e.g., sugars or sodium chloride), and other components consistent with pharmaceutical practice. The additives and carriers are selected such that they do not cause permanent damage to mammals.

The composition, intended for oral administration can be formulated in several forms including solid dosage forms such as capsules, tablets, or tea bags, and liquid dosage forms that can be enclosed in a sachet. The solid dosage form may be a capsule, which may be a soft or hard gelatin capsule, or a tablet, which may be a bilayer or trilayer tablet. Such bilayer or trilayer tablets can have an outer protective coating or finishing layer that encompasses the tablets. The outer protective coating layer, which is applied over the bilayer or trilayer tablets, may comprise any conventional coating formulations and may contain one or more film-formers or binders, such as hydrophilic polymers like hydroxypropyl methylcellulose (HPMC) and hydrophobic polymers like ethyl cellulose, cellulose acetate, polyvinyl alcohol-maleic anhydride copolymers, acrylic copolymers, beta-pinene polymers, and glyceryl esters of wood resins, among others. It may also contain one or more plasticizers, such as polyethylene glycol, triethyl citrate, diethyl phthalate, propylene glycol, glycerin, and butyl phthalate, among others. The film-formers are applied from a solvent system containing one or more solvents, including water, alcohols like methyl alcohol, ethyl alcohol, or isopropyl alcohol, ketones like acetone or ethyl methyl ketone, and chlorinated hydrocarbons like methylene chloride, dichloroethane, and 1,1,1-trichloroethane. Herein, the tablets are preferably formulated to have a weight within the range of about 4 grams to about 6 grams, while capsules are preferably formulated to have a weight range of about 250 milligrams (mg) to about 550 milligrams (mg). The tea bags are preferably formulated to have a weight of about 2 grams (g), and sachets are formulated to have a preferred weight of about 15 milliliters (mL). For oral administration, the dosage of the composition may vary depending on the condition being treated. A daily dosage of the composition may be given based on the formulation used. For instance, the composition formulated in a size 1 capsule cap may be given at a daily dosage of about 1000 to 1960 mg/day. Similarly, the composition formulated in a size 0 capsule cap may be given at a daily dosage of about 1000 to 1100 mg/day. For the composition formulated in a tea bag, a daily dosage of about 1 glass/day may be administered. Lastly, for the liquid formulation of the composition in sachet form, a daily dosage of about 15 milliliters may be given. It should be noted that the above dosage ranges are provided for illustrative purposes only and may be varied depending on various factors, including the age, weight, and medical condition of the patient. The scope of the invention is defined by the appended claims and is not limited by the specific examples provided herein.

The composition may be incorporated with one or more excipients that are considered pharmaceutically acceptable. As used herein, the term "excipient" refers to any non-therapeutic agent that serves as a carrier or vehicle for transporting therapeutic agents to a subject or is added to a pharmaceutical composition to enhance its storage, handling, or dose-forming properties. Excipients may include, but are not limited to, diluents, disintegrants, binding agents, adhesives, wetting agents, lubricants, glidants, surface modifiers, flavorings, fragrances, dyes, and other additives that improve the appearance or mask unpleasant tastes or odors. All such excipients can be used in any dosage form according to the present disclosure and may be in solid, semi-solid, liquid, or combined states. The preparation of compositions with excipients can be accomplished by any suitable pharmacy technique that involves mixing the excipient with a therapeutic agent or drug. In one embodiment, water may be used as an excipient for the liquid dosage form.

The composition may be incorporated with one or more binding agents or adhesives as excipients, especially for the solid dosage form. Such binding agents and adhesives are capable of providing sufficient cohesiveness to the powder being compressed into tablets to permit normal processing operations such as sizing, lubrication, compression, and packaging while allowing the tablet to disintegrate and the composition to be absorbed upon ingestion. Suitable binding agents and adhesives that can be used include but are not limited to, sucrose, gelatin, glucose, starch, or the like, alone or in combination.

The composition may include one or more sweeteners, particularly for the liquid dosage form. Examples of sweeteners that can be used include but are not limited to, aspartame, cyclamate, dextrose, isomaltose, maltitol, mannitol, saccharin, sorbitol, stevia, xylitol, or the like. Herein, it is preferable that the composition, as a whole, further contains 10 wt. % of sweeteners selected from the group consisting of sugar, honey, or stevia.

The present invention can be prepared utilizing conventional techniques commonly utilized in the pharmaceutical industry. Specific embodiments of the present invention may be utilized for the preparation of the composition, including but not limited to dry mixing, direct compression, milling, dry or non-aqueous granulation, wet granulation, or fusion for the production of solid dosage forms. The following embodiments disclosed herein provide a method of preparing the composition in various forms including capsules, tablets, tea bags, and liquid formulation in sachet form.

Embodiment 1

This composition for conditioning dampness-heat is in capsule form and contains active ingredients in specific ratios. The active ingredients include licorice root, forsythia shell, tree peony root bark, baical skullcap root, cassia twig, root of Chinese thorowax, *Oroxylum indicum* seed, mulberry leaf, prunella vulgaris, honeysuckle, and perilla leaf. The ratio of each ingredient is approximately 3:10:10:10:8:10:2:10:5:7:3. The capsules are formulated to weigh between about 250 to 280 mg and about 500 to 550 mg for size 1 and 0 capsule caps, respectively.

The method for producing the capsule form of the composition involves the following steps:

Raw material preparation: Firstly, the active ingredients are cleaned and measured in the specified ratio;

Heating: The measured raw materials of the active ingredients are heated within a temperature range of 120 to 140° C.;

Grinding: After heating, the active ingredients are ground into a powder form;

Capsule formation: Finally, the powder form of the active ingredients is inserted into capsule caps in accordance with the size of the capsule and the weight of the finished product.

The disclosed method offers a convenient and efficient means of producing the composition in capsule form, which may provide benefits such as ease of administration and improved bioavailability.

Embodiment 2

This composition for conditioning dampness-heat is in tablet form and contains active ingredients in specific ratios. The active ingredients include licorice root, forsythia shell, tree peony root bark, baical skullcap root, cassia twig, root of Chinese thorowax, *Oroxylum indicum* seed, mulberry leaf, prunella vulgaris, honeysuckle, and perilla leaf. The ratio of each ingredient is approximately 3:10:10:10:8:10:2:10:5:7:3. The tablets are formulated to weigh about 4 to 6 g.

The method for producing the tablet form of the composition comprises the following methods 1 and 2:

Method 1:

Raw material preparation: The active ingredients are cleaned and measured in the Heating: The measured raw materials of the active ingredients are heated within a temperature range of 120 to 140° C.;

Grinding: After heating, the active ingredients are ground into a powder form;

Tablet formation: The powder form of the active ingredients is compressed in tablet form in accordance with the size and weight of the finished product;

Coating: Finally, the finished product is coated with a sweetener or binding agent.

Method 2:

Raw material preparation: The active ingredients are cleaned and measured in the specified ratio;

Heating: The measured raw materials of the active ingredients are heated within a temperature range of 120 to 140° C.;

Grinding: After heating, the active ingredients are ground into a powder form;

Mixing: The powdered mixture is mixed with a liquid sweetener.

Tablet formation: The resulting solid mixture of the active ingredients is compressed in tablet form in accordance with the size and weight of the finished product.

The disclosed method offers a convenient and efficient means of producing the composition in tablet form, which may provide benefits such as ease of administration and improved bioavailability.

Embodiment 3

This composition for conditioning dampness-heat is in tea bag form and contains active ingredients in specific ratios. The active ingredients include licorice root, forsythia shell, tree peony root bark, baical skullcap root, cassia twig, root of Chinese thorowax, *Oroxylum indicum* seed, mulberry leaf, prunella vulgaris, honeysuckle, and perilla leaf. The ratio of each ingredient is approximately 3:10:10:10:8:10:2:10:5:7:3. The tea bags are formulated to weigh about 2 g.

The method for producing the tea bag form of the composition comprises the following steps:

Raw material preparation: The active ingredients are cleaned and measured in the Heating: The measured raw materials of the active ingredients are heated within a temperature range of 120 to 140° C.;

Grinding: After heating, the active ingredients are ground into a powder form;

Tea bag formation: Finally, the powder form of the active ingredients is inserted in a tea bag in accordance with the size and weight of the finished product.

The disclosed method offers a convenient and efficient means of producing the composition in tea bag form, which may provide benefits such as ease of administration and improved bioavailability.

Embodiment 4

This composition for conditioning dampness-heat is in liquid formulation in sachet form and contains active ingredients in specific ratios. The active ingredients include licorice root, forsythia shell, tree peony root bark, baical skullcap root, cassia twig, root of Chinese thorowax, *Oroxylum indicum* seed, mulberry leaf, prunella vulgaris, honeysuckle, and perilla leaf. The ratio of each ingredient is approximately 3:10:10:10:8:10:2:10:5:7:3. The sachets are formulated to weigh about 15 mL.

The method for producing the liquid formulation of the composition in sachet form involves the following steps:

Raw material preparation: The active ingredients are cleaned and measured according to the specified ratio;

Weighing: The active ingredients are weighed to a total weight of 620 g;

Heating and boiling: The weighed active ingredients are heated and boiled in 2.5 L of water within a temperature range of 120 to 140° C. until the water volume reduces to 1.5 L;

Sachet formation: Finally, the liquid of the active ingredients is filled into a sachet according to the desired size and weight of the finished product.

The disclosed method offers a convenient and efficient means of producing the composition in sachet form, which may provide benefits such as ease of administration and improved bioavailability.

An example illustrating the effectiveness of this composition in comparison to other conventional products for conditioning dampness-heat is provided below, however, it should not be viewed as limiting. In addition to the active ingredients, appropriate excipients, carriers, and optional flavorings or colorants may also be included in the formulation. The benefits of this invention are further elaborated in the following description.

Example 1

Experimental studies were conducted to evaluate the effects of the composition in the liquid formulation in sachet form, which is part of the present invention, for conditioning dampness-heat symptoms. The performance of this composition was compared against three conventional dampness-heat conditioning products, and the results of this comparison are presented in the following Table 2.

TABLE 2

Comparison of the Effects of the Composition of the Present Invention and Three Conventional Dampness-Heat Conditioning Products on Alleviating Symptoms Related to Dampness-Heat

| Dampness-heat Symptom Severity | Product | Dosage | Duration of Effectiveness |
|---|---|---|---|
| Mild | Composition of the present invention | 200 mL | 2-4 hours |
| | Gypsum fibrosum (e.g., The Three Legs Cooling Water; Cool Rhine) | 200 mL | 1-2 days |
| | Basil Seeds | 200 mL | 2-3 days |
| | Eight Treasures Herbal Tea | 200 mL | 1-2 days |
| Moderate | Composition of the present invention | 500 mL | 2-4 hours |
| | Gypsum fibrosum (e.g., The Three Legs Cooling Water; Cool Rhine) | 500 mL | 1-2 days |
| | Basil Seeds | 500 mL | 2-3 days |
| | Eight Treasures Herbal Tea | 500 mL | 1-2 days |

The result presented in the above Table 2 displays the efficacy of the composition of the present invention in comparison to other products for mild and moderate dampness-heat symptom severities, along with their respective dosages. For mild symptom severity, the composition of the present invention was administered at a dosage of 200 mL and demonstrated a duration of effectiveness of 2-4 hours. Other products such as *Gypsum fibrosum*, Basil Seeds, and Eight Treasures Herbal Tea were also administered at a dosage of 200 mL, but their duration of effectiveness was 1-2 days, 2-3 days, and 1-2 days, respectively. Therefore, it can be concluded that the composition of the present invention is more effective in conditioning mild symptoms of dampness-heat compared to the other products, as it showed a shorter duration of effectiveness at a lower dosage.

Similarly, for moderate symptom severity, the composition of the present invention was administered at a dosage of 500 mL and demonstrated a duration of effectiveness of 2-4 hours. Other products such as *Gypsum fibrosum*, Basil Seeds, and Eight Treasures Herbal Tea were also administered at a dosage of 500 mL, but their duration of effectiveness was 1-2 days, 2-3 days, and 1-2 days, respectively. Therefore, it can be concluded that the composition of the present invention is more effective in conditioning moderate symptoms of dampness-heat compared to the other products, as it showed a shorter duration of effectiveness at a lower dosage.

Overall, the results revealed that the composition of the present invention is more effective in treating dampness-heat symptoms compared to the other products, as it demonstrated a shorter duration of effectiveness at a lower dosage.

Example 2

An experimental investigation was carried out to assess the effectiveness of the liquid formulation in sachet form, which forms part of the present invention, in reducing cough symptoms associated with dampness-heat. Traditional Chinese Medicine (TCM) attributes coughing to a disturbance in the body's Qi, which may be associated with different disharmony patterns, including dampness-heat. Specifically, the study sought to demonstrate the effectiveness of this composition in alleviating cough symptoms related to dampness-heat among patients diagnosed with Coronavirus disease 2019 (COVID-19) and compared its performance against three conventional dampness-heat conditioning products. The results of this comparison are presented in Table 3.

TABLE 3

Comparison of the Effects of the Composition of the Present Invention and Three Conventional Dampness-Heat Conditioning Products in Alleviating Dampness-Heat Cough Symptoms in COVID-19 Patients

| Subject | Product | Dosage | Duration of Effectiveness in 3-6 hours (Cough measured by frequency in 15-minute intervals) |
|---|---|---|---|
| COVID-19 Patients with dampness-heat cough symptoms | Composition of the present invention | 200 mL | Significant reduction in cough by 50% and phlegm by 50%, with a change in phlegm color from green to white |
| | Gypsum fibrosum (e.g., The Three Legs Cooling Water; Cool Rhine) | 200 mL | Reduction in cough by 5% or less |
| | Basil Seeds | 200 mL | Reduction in cough by 5% or less |
| | Eight Treasures Herbal Tea | 200 mL | Reduction in cough by 5% or less |

Table 3 presents a comparison of the effectiveness of the composition of the present invention in liquid formulation against three conventional dampness-heat conditioning products in reducing cough symptoms related to dampness-heat in COVID-19 patients. The dosage for each product was 200 mL, and the duration of effectiveness was measured in 15-minute intervals for 3-6 hours.

The results show that the composition of the present invention was able to reduce cough frequency and phlegm production by 50%, with a notable change in phlegm color from green to white. In contrast, the three conventional products, including *Gypsum fibrosum* (e.g., The Three Legs Cooling Water; Cool Rhine), Basil Seeds, and Eight Treasures Herbal Tea, showed only a 5% or less reduction in cough frequency.

The results indicated that the composition of the present invention is more effective in alleviating cough symptoms related to dampness-heat in COVID-19 patients compared to traditional dampness-heat conditioning products.

While this invention has been described by reference to certain specific embodiments and examples, it will be understood that this invention is capable of further modifications. This application is, therefore, intended to cover any variations, uses, or adaptations of the invention following the general principles thereof, and including such departures from the present disclosure as come within the known or customary practice in the art to which this invention pertains and falls within the limits of the appended claims.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications, and variations that fall within the scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. A pharmaceutical composition for conditioning dampness-heat consisting of licorice root, forsythia shell, tree peony root bark, baical skullcap root, cassia twig, root of Chinese thorowax, *Oroxylum indicum* seed, mulberry leaf, prunella vulgaris, honeysuckle and perilla leaf.

2. The pharmaceutical composition as claimed in claim 1, wherein the ratio of said licorice root to said forsythia shell to said tree peony root bark to said baical skullcap root to said cassia twig to said root of Chinese thorowax to said *Oroxylum indicum* seed to said mulberry leaf to said prunella vulgaris to said honeysuckle and to said perilla leaf is about 3:10:10:10:8:10:2:10:5:7:3.

3. The pharmaceutical composition as claimed in claim 1, wherein said licorice root, said forsythia shell, said tree peony root bark, said baical skullcap root, said cassia twig, said root of Chinese thorowax, said *Oroxylum indicum* seed, said mulberry leaf, said prunella vulgaris, said honeysuckle and said perilla leaf is a heated licorice root, heated forsythia shell, heated tree peony root bark, heated baical skullcap root, heated cassia twig, heated root of Chinese thorowax, heated *Oroxylum indicum* seed, heated mulberry leaf, heated prunella vulgaris, heated honeysuckle and heated perilla leaf.

4. The pharmaceutical composition as claimed in claim 1, wherein said pharmaceutical composition further consists of 10 wt. % of sweeteners selected from the group consisting of sugar, honey or stevia.

5. The pharmaceutical composition as claimed in claim 1, wherein said pharmaceutical composition is an oral composition.

6. The pharmaceutical composition as claimed in claim 1, wherein said pharmaceutical composition is formulated in the form of tablets, capsules, tea bags or sachets.

7. The pharmaceutical composition as claimed in claim 6, wherein said tablets further include an outer protective coating or finishing layer surrounding said tablets.

8. The pharmaceutical composition as claimed in claim 6, wherein said tablets have a weight from about 4 grams to about 6 grams.

9. The pharmaceutical composition as claimed in claim 6, wherein said capsules have a weight from about 250 milligrams to about 280 milligrams or from about 500 milligrams to about 550 milligrams.

10. The pharmaceutical composition as claimed in claim 6, wherein said tea bags have a weight of about 2 grams.

11. The pharmaceutical composition as claimed in claim 6, wherein said sachets have a weight of about 15 milliliters.

* * * * *